US00PP19473P3

(12) United States Plant Patent
Nicolaïet al.

(10) Patent No.: US PP19,473 P3
(45) Date of Patent: Nov. 25, 2008

(54) APPLE TREE NAMED 'ZARI'

(50) Latin Name: *Malus domestica*
Varietal Denomination: ZARI

(75) Inventors: Johan Nicolaï, Sint-Truiden (BE); Paul Van Laer, Heks (BE); Johan Keulemans, Korbeek-Lo (BE); Hendrik Eyssen, Holsbeek (BE); Els Pauwels, Amougies (BE); Inge De Wit, Lovenjoel (BE)

(73) Assignee: Better3Fruit N.V., Heverlee (BE)

( * ) Notice: Subject to any disclaimer, the term of this patent is extended or adjusted under 35 U.S.C. 154(b) by 0 days.

(21) Appl. No.: 11/529,551

(22) Filed: Sep. 29, 2006

(65) Prior Publication Data

US 2007/0113309 P1 May 17, 2007

(30) Foreign Application Priority Data

Nov. 16, 2005 (EP) ..... 2005/2293

(51) Int. Cl.
*A01H 5/00* (2006.01)

(52) U.S. Cl. ..... Plt./172
(58) Field of Classification Search ..... Plt./172
See application file for complete search history.

(56) References Cited

PUBLICATIONS

Bettter3Fruit N.V. website–http://www.better3fruit.com publication of "Apple 2" on Dec. 15, 2004 (1 page).
Better3Fruit N.V. website–http://www.better3fruit.com publication entitled "Products on the market–ZARI" on Nov. 8, 2005 (1 page).

*Primary Examiner*—Anne Marie Grunberg
*Assistant Examiner*—Louanne C Krawczewicz My
(74) *Attorney, Agent, or Firm*—Foley & Lardner, LLP

(57) ABSTRACT

A new and distinct apple tree named 'ZARI' particularly characterized by having early maturity of fruit (about 2 weeks earlier than 'Gala'); good storability of fruit; good shelf life of fruit; and very crisp and juicy pulp of fruit.

3 Drawing Sheets

Priority claim

This application claims priority under 35 U.S.C. § 119(f) of the European Community Plant Variety Rights No. 2005/2293 filed Nov. 16, 2005.

Latin name of the genus and species of the plant claimed: *Malus domestica.*

Variety denomination: 'ZARI'.

BACKGROUND OF THE INVENTION

The present invention relates to a new and distinct variety of apple tree, botanically known as *Malus domestica*, of the Family *Rosaceae*, and hereinafter referred to by the variety name 'ZARI'.

The new *Malus* variety is a product of a planned breeding program conducted by the inventors, Johan Nicolai, Paul Van Laer, Johan Keulemans, Hendrik Eyssen, Els Pauwels and Inge De Wit. The objective of the breeding program was to develop a new *Malus* variety which produced fruit with a crisp and juicy pulp, as well as, good storage capacity and shelf life.

The new *Malus* variety 'ZARI' originated from a cross made in a planned, controlled breeding program in Rillaar, Belgium in 1988. The female or seed parent is the *Malus domestica* variety 'ELSTAR' (patented, U.S. Plant Pat. No. PP6,450 and Plant Breeder's Rights Nos.: BE 90002, DE APF 00007, FR 10412, GB 900030 and NL APP0060). The male or pollen parent is the *Malus domestica* variety 'DELCORF' (patented, Plant Breeder's Rights No. FR. 112364).

The new seedling variety 'ZARI' was first fruited and selected for propagation and further testing by the inventors in 1994 in a controlled environment in Fernelmont (Franc-Waret), Belgium. Asexual reproduction of the new variety by grafting onto M9 rootstocks, was first performed in the winter of 1994–1995 in Gorsem, Belgium. Additional selection and asexual reproduction by the inventors occurred in 1999 and 2004 in Rillaar, Belgium. Asexual reproduction of 'ZARI' has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'ZARI' which in combination distinguish this apple tree as a new and distinct variety:

1. early maturity of fruit (about 2 weeks earlier than 'Gala');
2. good storability of fruit;
3. good shelf life of fruit; and
4. very crisp and juicy pulp of fruit.

In comparison to the parental varieties, 'ELSTAR' and 'DELCORF', the new variety 'ZARI' differs primarily in the traits listed in Table 1.

TABLE 1

| Characteristic | New Variety 'ZARI' | Female Parent 'ELSTAR' (PP6,450) | Male Parent 'DELCORF' |
|---|---|---|---|
| Fruit Shape | Oblong conical | Conic to slightly oblong | Globose conical |
| Fruit Skin Color | Yellow-green | Yellow-orange | Yellow |
| Overcolor of Fruit | Orange-red | Orange, red striped | Orange-red, striped |
| Flesh Color | Yellow | Creamy-white tinged with yellow. | Cream |

Of the commercial varieties known to the inventor, the most similar in comparison to 'ZARI' is the parental variety 'DELCORF' as compared in Table 1. In addition, the fruit of 'ZARI' is sweeter and has a better storability and shelf life than the fruit of 'DELCORF'.

BRIEF DESCRIPTION OF THE DRAWINGS

The accompanying photographs illustrate the overall appearance of the new apple tree 'ZARI' showing the colors as true as is reasonably possible with color reproductions of this type. Colors in the photographs may differ slightly from the color values cited in the detailed botanical description, which accurately describe the color of 'ZARI'.

DETAILED BOTANICAL DESCRIPTION

Figure 1:
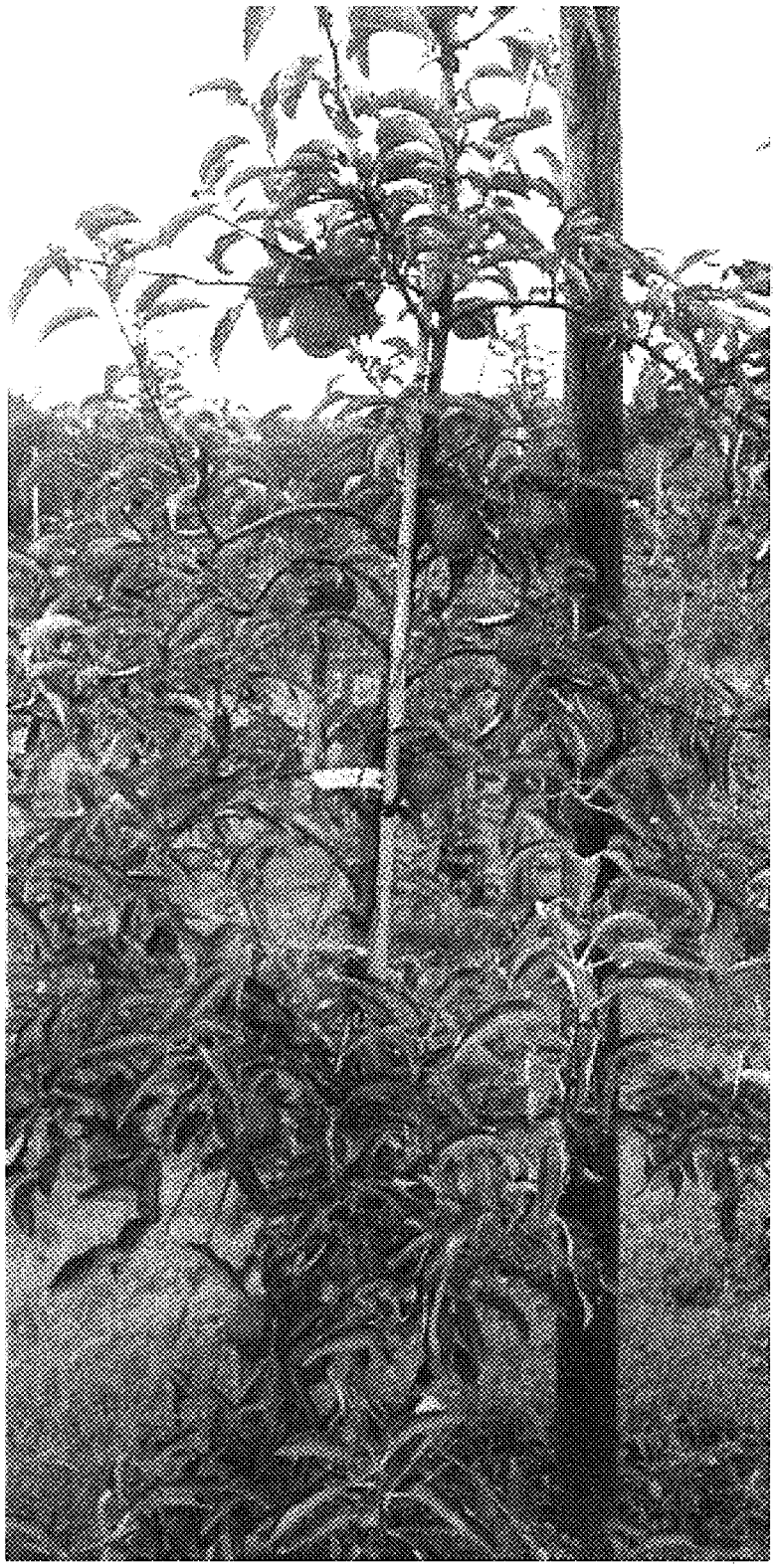
FIG. 1 shows a fruit bearing tree of 'ZARI' in the sixth growing season in August.
Figure 2:
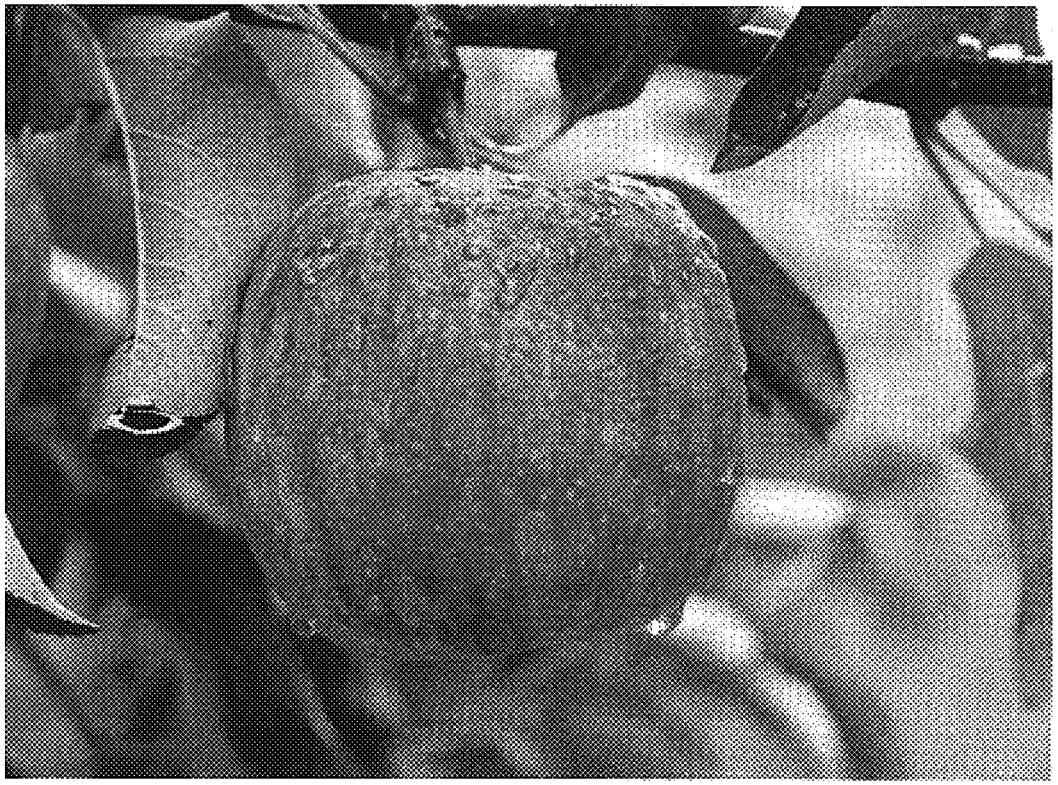
FIG. 2 shows a close-up view of the fruit, leaves and branches of 'ZARI' in the seventh growing season in August.
Figure 3:
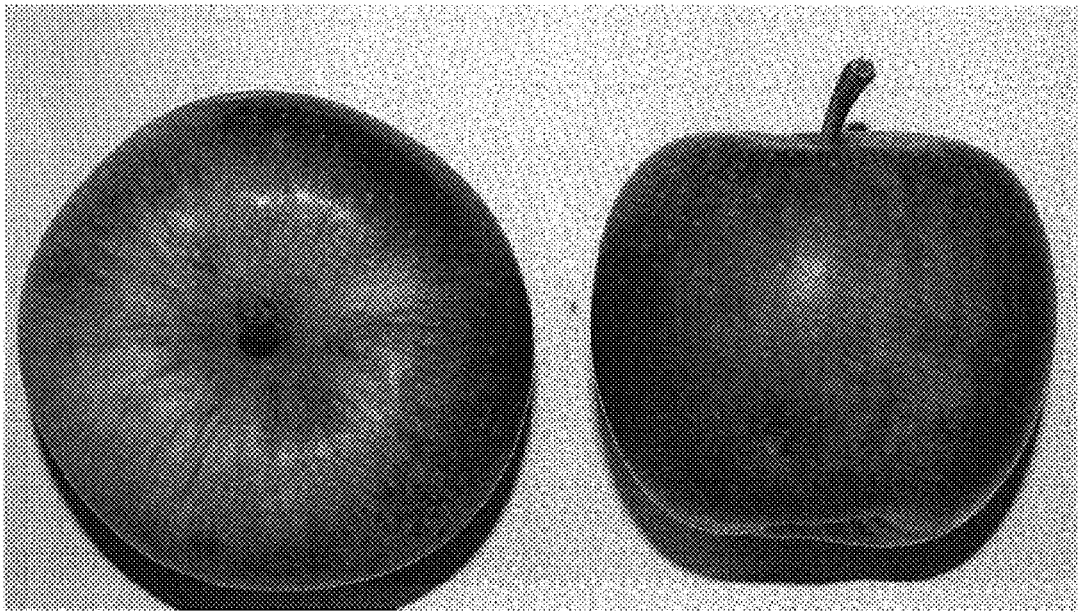
FIG. 3 shows a close-up view of mature fruit of 'ZARI'.
Figure 4:
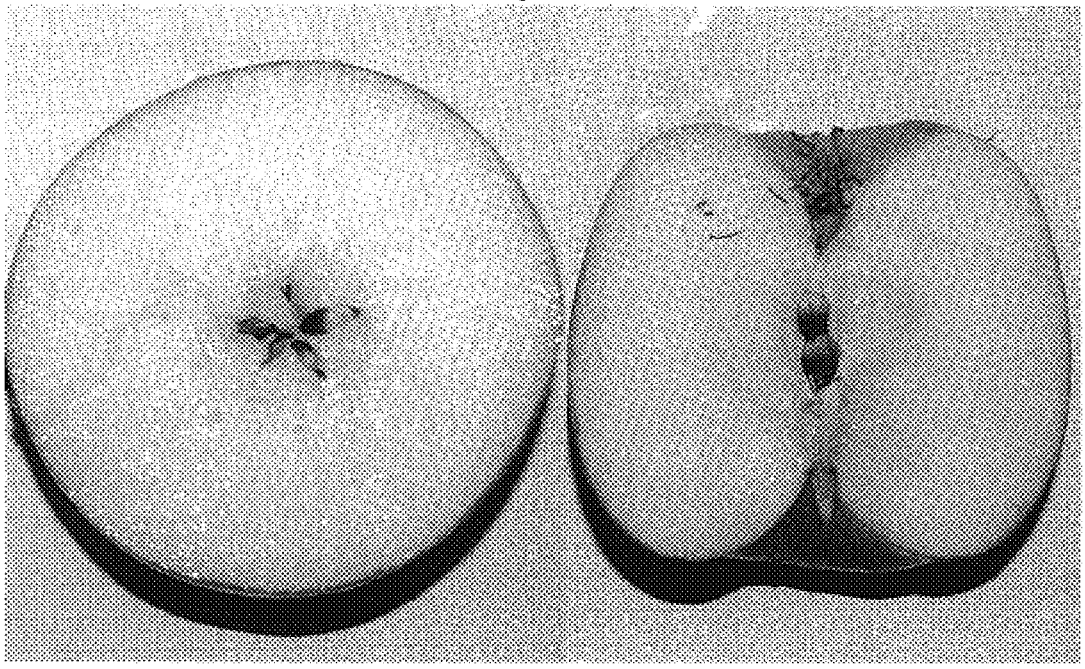
FIG. 4 shows dissection views of mature fruit of 'ZARI'.

'ZARI' has not been observed under all possible environmental conditions. The phenotype of the new variety may vary with variations in environment such as temperature, light intensity, and day length without any change in the genotype of the plant.

The aforementioned photographs, together with the following observations, measurements and values describe trees of 'ZARI' as grown in the apple nursery in Rillaar, Belgium, under conditions which closely approximate those generally used in commercial practice.

Unless otherwise stated, the detailed botanical description includes observations, measurements and values based on five (5) year old 'ZARI' trees grown in the apple nursery in Rillaar, Belgium, from 2002 to 2006. Quantified measurements are expressed as an average of measurements taken from a number of trees of 'ZARI'. The measurements of any individual tree, or any group of trees, of the new variety may vary from the stated average.

Color references are made to The Royal Horticultural Society Colour Chart (R.H.S.; 4th edition, 2001), except where general colors of ordinary significance are used. Color values were taken under daylight conditions at approximately 3:00 p.m. in Rillaar, Belgium.

Classification:

*Botanical.*—*Malus domestica.*

Parentage:

*Female or seed parent.*—*Malus domestica* cultivar 'ELSTAR' (patented, U.S. Plant Pat. No. 6,450 and Plant Breeder's Rights Nos.: BE 90002, DE APF 00007, FR 10412, GB 900030 and NL APP0060).

*Male or pollen parent.*—*Malus domestica* cultivar 'DELCORF' (patented, Plant Breeder's Rights No. FR 112364).

Propagation:

*Type.*—Bench-grafting to M9 rootstocks.

*Locality where grown and observed.*—Rillaar, Belgium.

Growing conditions:

*Light intensities.*—Full sunlight.

*Temperature.*—During day, grown in range of 2° C. to 23° C., and during evening, grow in range of −5° C. to 13° C. (based on the average month temperature).

Tree:

*Age.*—Observed trees were five years old.

*Vigor.*—Vigorous growth. About 22.19 cm +/−7.63 cm of terminal growth per year.

*Form.*—Ramified and orthotropic spreading; branch angle is about 82°.

*Branching habit.*—Main branches angle is 82.75° +/−7.34° with respect to trunk if allowed to grow naturally.

*Cropping behavior.*—Average beginning production; good and constant production and flowering.

*Density.*—About 2200 trees per hectare.

*Production.*—7.7 kg. per tree.

*Size at maturity.*—Height: 254 mm +/−28.36 mm. Spread: 174 mm +/−16.98 mm. Trunk Diameter (at 20 cm above graft union): 36.93 mm +/−3.71 mm.

*Surface texture.*—Very rough.

*Bark color.*—RHS 166A, greyed-orange.

*Trunk lenticels.*—Length: 1.64 mm +/−0.15 mm. Width: 3.23 mm +/−0.48 mm. Color: RHS 158C, yellow-white. Density: About 2 per $cm^2$.

Branches:

*Number per tree.*—About 32.

*Length.*—Varies due to shape of tree; up to a maximum of 101 cm +/−24.17 cm.

*Diameter* (*at 20 cm from the main stem*).—14.48 mm +/−2.01 mm.

*Surface texture.*—Rough.

*Color.*—Mature (after about 3 years old): RHS 166A, greyed-orange. New Growth: RHS 187A, greyed purple.

*Internode length.*—41.53 mm +/−9.15 mm.

*Internode diameter.*—11.8 mm +/−4.2 mm.

*Branch lenticels.*—Length: 1.34 mm +/−0.23 mm. Width: 2.25 mm +/−0.32 mm. Shape: Oval. Color: RHS 158C, yellow-white. Density: About 2 per $cm^2$.

Leaves:

*Arrangement.*—Alternate.

*Size.*—Length: 11.28 mm +/−0.23 mm. Width: 5.98 mm +/−0.32 mm. Thickness: 0.25 mm +/−0.03 mm.

*Overall shape.*—Ovate, petiolated.

*Base shape.*—Rounded.

*Apex shape.*—Acute.

*Margin.*—Serrate.

*Texture.*—Upper surface: Glabrous. Lower Surface: Weak pubescence.

*Pubescence.*—Upper surface: None. Lower Surface: Slight.

*Attitude in relation to shoot.*—Outwards.

*Color.*—Mature leaves, upper surface: RHS 136B, green. Mature leaves, lower surface: RHS 137D, green. Immature leaves: RHS 144A, yellow-green (upper and lower surface).

*Venation.*—Type: Pinnate. Color: Upper surface: RHS 144B, yellow-green. Lower surface: RHS N144D, yellow-green.

*Petiole.*—Length: 3.05 mm +/−0.33 mm. Diameter: 2.16 mm +/−0.15 mm. Color: RHS 178A, greyed-red.

*Stipule.*—Arrangement: free standing. Length (distance of stipules from basal attachment of petiole): _7.12 mm +/−1.81 mm. Width: 1.57 mm +/−0.55 mm.

*Spur.*—Present: Yes. Distance between each spur: 38.35 mm +/−7.65 mm. Number of fruit per spur: 1.

Inflorescence:

*Time of beginning of flowering.*—Medium (similar to 'Golden Delicious').

*Blooming period.*—Short to medium.

*Fragrance.*—Slight.

*Inflorescence size.*—Depth: 47.76 mm +/−5.81 mm (including pedicel). Diameter: 82.38 mm +/−8.75 mm.

*Number of flowers per inflorescence.*—5.1 +/−0.31.

*Flower size.*—Depth: 38.25 mm +/−5.2 mm (including pedicel). Diameter: 46.65 mm +/−3.28 mm. 60.48 mm +/−2.54 mm (with petals pressed down in horizontal position).

*Buds.*—Quantity: About 1 per spur. Shape: Pointed. Arrangement: Alternate. Length: 11.78 mm +/−0.98 mm. Width: 5.17 mm +/−0.37 mm. Texture: Smooth, moderate pubescence. Color: RHS 178A, greyed-red.

*Petals.*—Number per flower: 5. Arrangement: Overlapping. Length: 21.93 mm +/−2.59 mm. Width: 14.89 mm +/−1.65 mm. Overall shape: Obovate. Apex shape: Rounded. Base shape: Cunate. Texture: Smooth (both surfaces). Margin: Entire. Color: Open Flower Stage: Upper surface: RHS 70C, red-purple. Lower surface: RHS N66C, red-purple. Balloon stage: RHS N57D, red-purple.

*Sepals.*—Number per flower: 5. Length: 9.84 mm +/−1.87 mm. Width: 2.73 mm +/−0.47 mm. Overall Shape: Triangular. Apex Shape: Acute. Base Shape: Truncate. Texture: Sligthly rough (both surfaces). Margin: Entire. Color: RHS 143C, green (both surfaces).

*Pedicel.*—Length: 32.48 mm +/−4.91 mm. Diameter: 1.17 mm +/−0.19 mm. Texture: Weak pubescence. Color: RHS N199C (grey-brown) and RHS 143C (green).

Fruit:

*Keeping quality.*—Very good for an early variety. The fruit keeps well on the tree. It can be stored in cold temperature conditions for up to 6 weeks without loosing firmness and juiciness. It has a shelf life up to 2 weeks without loosing firmness and juiciness.

*Maturity when described.*—After 3 months in storage.

*Maturity period after full bloom.*—About 4 months after full bloom.

*Date of picking.*—Very early (end of August) (about 2 weeks earlier than 'Gala').

*Yield.*—Medium productivity, slight tendency to biennial bearing.

*Shape.*—Oblong conical.

*Appearance.*—Weak ribbing.

*Size.*—Height: 54.71 mm +/−2.54 mm. Width: 62.96 mm +/−1.82 mm. Weight: 113.2 g +/−4.66 g.

*Eye.*—Aperature: Fully open. Size: 8.03 mm +/−1.13 mm.

*Stem.*—Length: 36.23 mm +/−3.82 mm. Width: 1.75 mm +/−0.12 mm. Color: RHS 178A, greyed-red.

*Basin.*—Shape: Deep, pronounced. Depth: 0.90 mm +/−0.14 mm. Width: 2.59 mm +/−0.23 mm.

*Stalk cavity.*—Depth: 1.38 mm +/−0.2 mm. Width: 2.87 mm +/−0.22 mm. Shape: Medium, rounded.

*Crowning at calyx end.*—Medium.

*Skin.*—Appearance: Thin, slightly tough, slow to become oily in cold storage, russeted at stalk cavity, no tendency to crack, no bloom. Thickness: 0.21 mm +/−0.02 mm. Texture: Slightly rough. Overcolor of the skin: RHS N34A, orange-red. Percentage of skin surface with overcolor: About 75%. Pattern of overcolor: Striped. Background color of the skin: RHS 154A, yellow-green.

*Lenticels.*—Length: About 1.66 +/−0.35 mm. Width: About 0.96 +/−0.21 mm. Color: RHS 152A, yellow-green. Density: 4.01 +/−1.18 $cm^2$.

*Flesh.*—Color: RHS 11C, yellow. Texture: Crisp and juicy. Aroma: Strong. Eating quality: Very good. Firmness (at harvest, eat ripe): 7.28 +/−0.65 $kg/cm^2$. Soluble solids/Sugar content (at harvest, eat ripe): 15.43 +/−1.06% Brix. Acidity (at harvest, eat ripe): 9.3 g/l Malic acid.

*Core.*—Symmetry of core: conical. Distinctness of core lines: weak.

*Locules.*—Number (per fruit): 5. Length: 15.47 mm +/−1.67 mm. Width: 8.24 mm +/−1.08 mm. Form: oval. In transverse section: Slightly open (5%).

*Seeds.*—Number per fruit: 4.80 +/−1.79. Shape: Ellipsoid, elongated and pointed. Length: 8.99 mm +/−0.47 mm. Width: 4.58 mm +/−0.28 mm. Color: RHS 200C, brown.

Reproductive organs:

*Androecium.*—Stamen: Number per flower: 17.2 +/−2.86 mm. Filament: Length: 5.70 mm +/−1.4 mm. Anther: Length: 2.46 mm +/−0.19 mm. Diameter: 1.67 mm +/−0.19 mm. Color: RHS 11C, yellow. Pollen: Amount: Moderate. Color: RHS 10A, yellow. Pollinators: 'Gala', 'Golden Gem', 'Hillieri'.

*Gynoecium.*—Pistils: Number per flower: 5. Length: 10.37 mm +/−0.85 mm. Stigma: Shape: Bulbous on top. Position: Above anthers. Color: RHS 151B, yellow-green. Style: Color: RHS 151B, yellow-green.

Use: Fresh market.

Disease/pest resistance: No known resistance.

Winter hardiness: Tolerant to temperatures down to min. −10° C. without observed damage to wood and buds of dormant apple trees.

Drought/heat tolerance: Tolerant to temperatures up to min 40° C., growth is limited by drought periods without irrigation.

We claim:

1. A new and distinct apple tree plant named 'ZARI', substantially as illustrated and described herein.

* * * * *